United States Patent [19]

VandenBerg

[11] Patent Number: Plant 6,581

[45] Date of Patent: Feb. 7, 1989

[54] CHRYSANTHEMUM PLANT NAMED YELLOW OVARO

[75] Inventor: Cornelis P. VandenBerg, Salinas, Calif.

[73] Assignee: Yoder Brothers, Inc., Barberton, Ohio

[21] Appl. No.: 49,952

[22] Filed: May 15, 1987

[51] Int. Cl.[4] ..... A01H 5/00

[52] U.S. Cl. ..... Plt./78

[58] Field of Search ..... Plt. 78

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Yellow Ovaro particularly characterized by its flat capitulum form; anemone capitulum type; yellow ray floret color; diameter across face of capitulum of up to 12 cm at maturity when grown as a pinched disbudded pot mum, with diameter of anemone cushion of up to 4 cm; uniform eight week photoperiodic flowering response to short days; tall plant height when grown as a pinched pot mum; recommended both as disbudded and spray pot mum; and spreading and prolific branching pattern.

3 Drawing Sheets

The present invention comprises a new and distinct cultivar of Chrysanthemum, botanically known as *Chrysanthemum morifolium,* Ramat., and referred to by the cultivar name Yellow Ovaro.

Yellow Ovaro, identified as 79U03C04, is a product of a mutation induction program which had the objective of creating new chrysanthemum cultivars that would expand the color range of an existing cultivar while retaining all other traits.

Yellow Ovaro was discovered and selected by a technician working under guidelines established by Cornelis P. VandenBerg on Mar. 25, 1984 in a controlled environment in Alva, Fla. as one flowering plant within a flowering from stock plants which had been exposed as unrooted cuttings block established as unrooted cuttings to an X-ray source of 1750 rads. The irradiated parent was the cultivar identified as Ovaro, disclosed, in a pending plant patent application.

The first act of asexual reproduction of Yellow Ovaro was accomplished when vegatative cuttings were taken from the initial selection in June of 1984 in a controlled environment in Alva, Fla., by technicians working under formulations established and supervised by Cornelis P. VandenBerg.

Horticultural examination of controlled flowerings of successive plantings has shown that the unique combination of characteristics as herein disclosed for Yellow Ovaro are firmly fixed and are retained through successive generations of asexual reproduction.

Yellow Ovaro has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Yellow Ovaro, which, in combination, distinguish this Chrysanthemum as a new and distinct cultivar:

1. Flat capitulum form.
2. Anemone capitulum type.
3. Yellow ray floret color.

4. Diameter across face of capitulum up to 12 cm at maturity, when grown as a pinched disbudded pot mum, with the diameter of the anemone cushion being up to 4 cm.
5. Uniform eight week photoperiodic flowering response to short days.
6. Tall plant height, requiring no long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Spreading and prolific branching pattern.

The accompanying photogrpahic drawings show typical inflorescence and leaf characteristics of Yellow Ovaro, with the colors being as nearly true as possible with illustrations of this type.

Sheet 1 is a color photograph of Yellow Ovaro grown as a pinched disbudded pot mum.

Sheet 2 is a black and white photograph of three views of the inflorescence of Yellow Ovaro.

Sheet 3 is a black and white photograph showing the upper and under sides of the leaves of Yellow Ovaro at the three stages of development (mature, intermediate and immature).

Of the commercial cultivars known to the inventor, the most similar in comparison to Yellow Ovaro is the parent cultivar Ovaro. All traits of Yellow Ovaro are similar to those of Ovaro, except the color of ray florets. The color of the ray florets of Yellow Ovaro is clear yellow, as contrasted with the lighter yellow with bronze overcast ray florets of Ovaro.

In the following description color references are made to The Royal Horticultural Society Color Chart. The color values were determined on plant material grown as a pinched disbudded pot mum in Salinas, Calif. on Dec. 12. 1986.

Classification:

*Botanical.*—*Chrysanthemum morifolium,* Ramat., cv Yellow Ovaro.

*Commercial.*—Anemone disbudded pot mum.

INFLORESCENCE

A. Capitulum:
*Form.*—Flat.
*Type.*—Anemone.
*Diameter across face.*—Up to 12 cm at maturity, with diameter of anemone cushion of up to 4 cm.

B. Corolla of ray florets:
*Color (general tonality from a distance of three meters).*—Yellow.
*Color (upper surface).*—6A to 7A.
*Color (under surface).*—6C to 7C.
*Shape.*—Flat, oblong.

C. Corolla of disc florets:
*Color (mature).*—14A to 14B.
*Color (immature).*—154A.

D. Reproductive organs:
*Androecium.*—Present in disc florets only, scant pollen.
*Gynoecium.*—Present in both ray and disc florets.

PLANT

A. General appearance:

*Height.*—Tall; 25 to 35 cm as a pinched disbudded pot mum with no long days after pinch prior to short days and 1 application of 2500 ppm B-9 SP.
*Branching pattern.*—Spreading and prolific.

B. Foliage:
*Color (upper surface).*—137A.
*Color (under surface).*—138B.
*Shape.*—Lobed and slightly serrated.

I claim:

1. A new and distinct Chrysanthemum plant named Yellow Ovaro, as described and illustrated, and particularly characterized as to uniqueness by the combined characteristics of flat capitulum form; anemone capitulum type; yellow ray floret color; diameter across face of capitulum of up to 12 cm at maturity when grown as a pinched disbudded pot mum, with diameter of anemone cushion of up to 4 cm; uniform eight week photoperiodic flowering response to short days; tall plant height when grown as a pinched pot mum; recommended both as disbudded and spray pot mum; and spreading and prolific branching pattern.

* * * * *

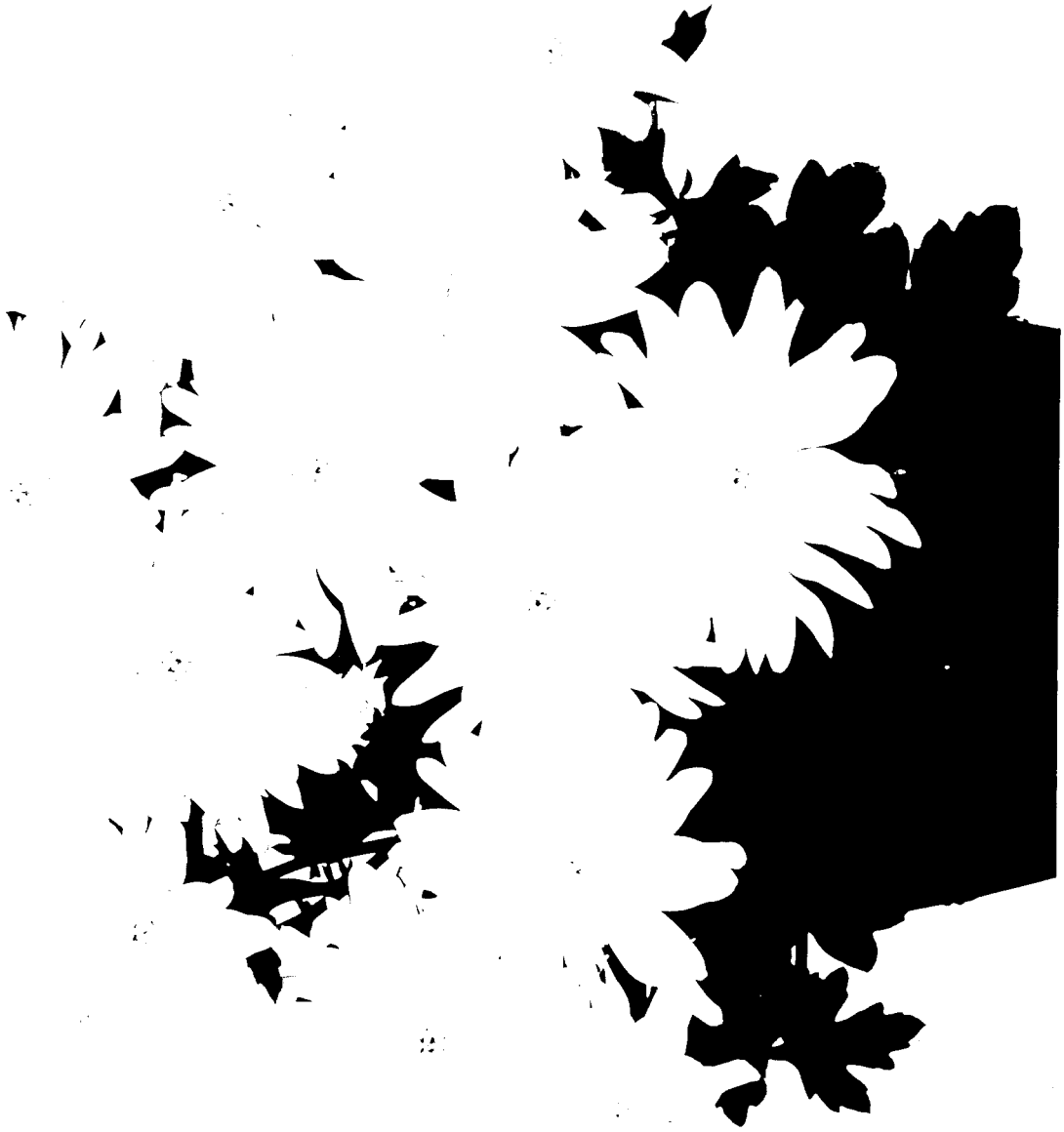

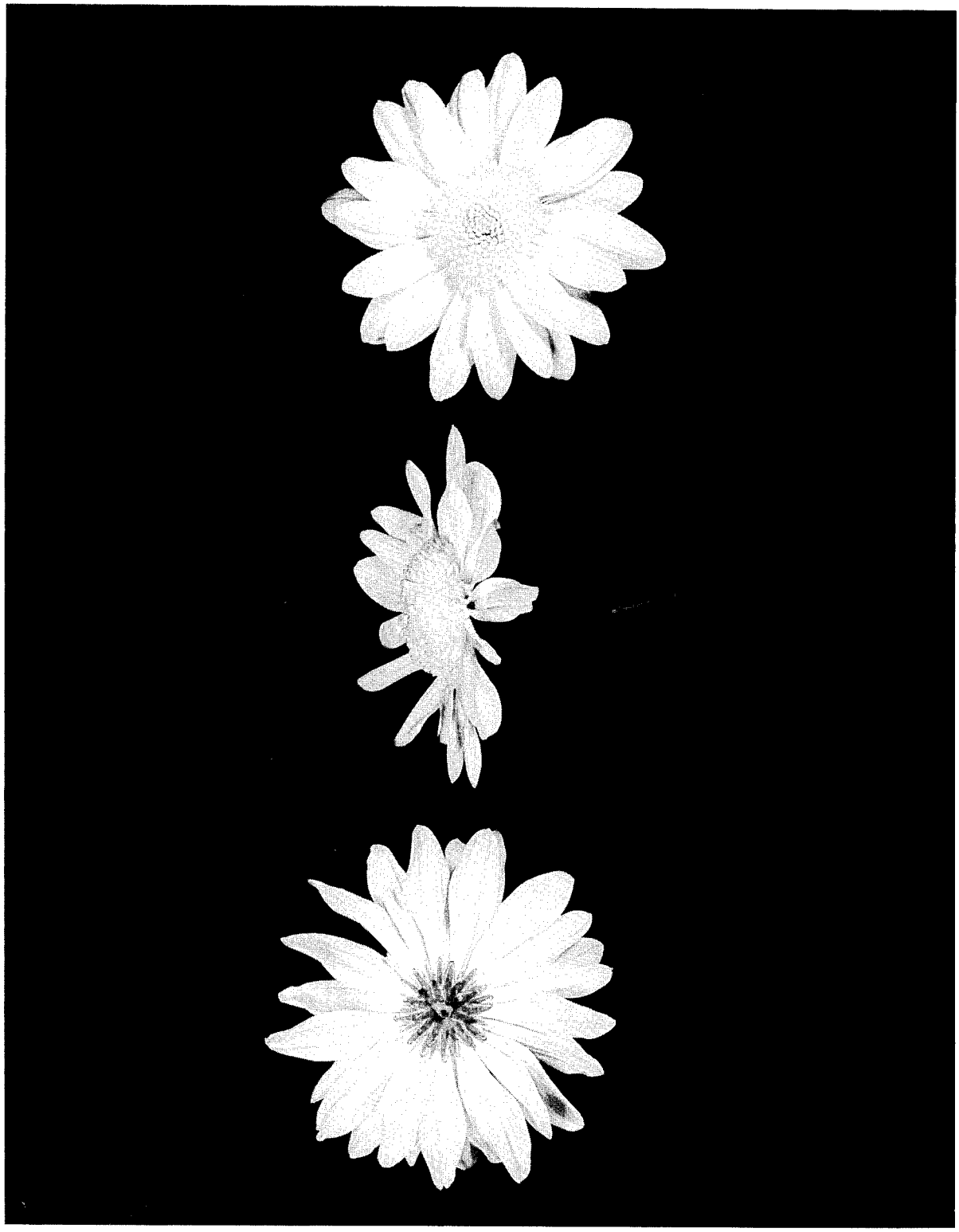

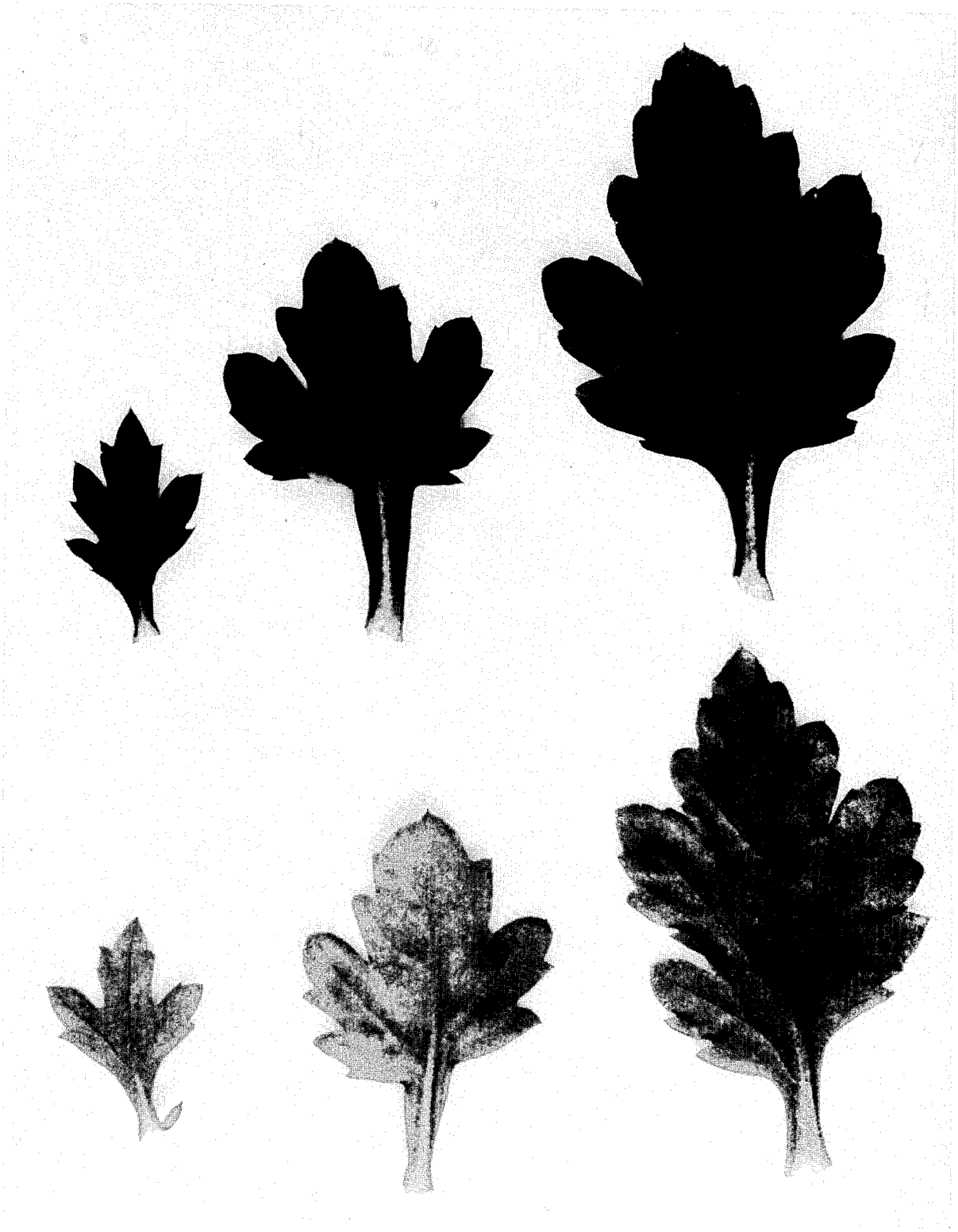

UNITED STATES PATENT AND TRADEMARK OFFICE

CERTIFICATE OF CORRECTION

PATENT NO. : PP 6,581

DATED : February 7, 1989

INVENTOR(S) : Cornelis P. VandenBerg

It is certified that error appears in the above—identified patent and that said Letters Patent is hereby corrected as shown below:

Column 1, Line 14, after "flowering" the phrase "block established as rooted cuttings" should be inserted.

Column 2, line 15, "photogrpahic" should be "photographic".

Signed and Sealed this

Third Day of July, 1990

*Attest:*

HARRY F. MANBECK, JR.

*Attesting Officer*

*Commissioner of Patents and Trademarks*